United States Patent
Petrick et al.

(10) Patent No.: US 6,457,861 B1
(45) Date of Patent: Oct. 1, 2002

(54) METHOD AND APPARATUS FOR CORRECTING ELECTRONIC OFFSET AND GAIN VARIATIONS IN A SOLID STATE X-RAY DETECTOR

(75) Inventors: Scott Petrick, Sussex; Swami Narasimhan, Waukesha; Habib Vafi, Brookfield, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1 day.

(21) Appl. No.: 09/713,730

(22) Filed: Nov. 15, 2000

(51) Int. Cl.[7] .......................... G01D 18/00; A61B 6/03
(52) U.S. Cl. ........................................ 378/207; 378/4
(58) Field of Search ...................... 378/207, 4

(56) References Cited

U.S. PATENT DOCUMENTS 5,999,588 A * 12/1999 Shao et al. ................. 378/4
6,325,539 B1 * 12/2001 Bromberg et al. .......... 378/4

* cited by examiner

Primary Examiner—Drew A. Dunn
(74) Attorney, Agent, or Firm—McAndrews, Held & Malloy, Ltd.; Peter J. Vogel; Michael A. Dellapenna

(57) ABSTRACT

A method and apparatus for correcting electronic offset and gain variations in solid state x-ray detectors includes dedicating rows at the end of an x-ray detector scan. The dedicated rows may be used to measure the "signal" induced by electronic offset and gain variations in solid state x-ray detectors. The first row may be used to measure the signal induced by electronic offset. The second row may be used to measure to signal induced by gain variations. Measurements of the induced signals taken from the dedicated rows may be used to eliminate structured artifacts from the x-ray image.

31 Claims, 7 Drawing Sheets

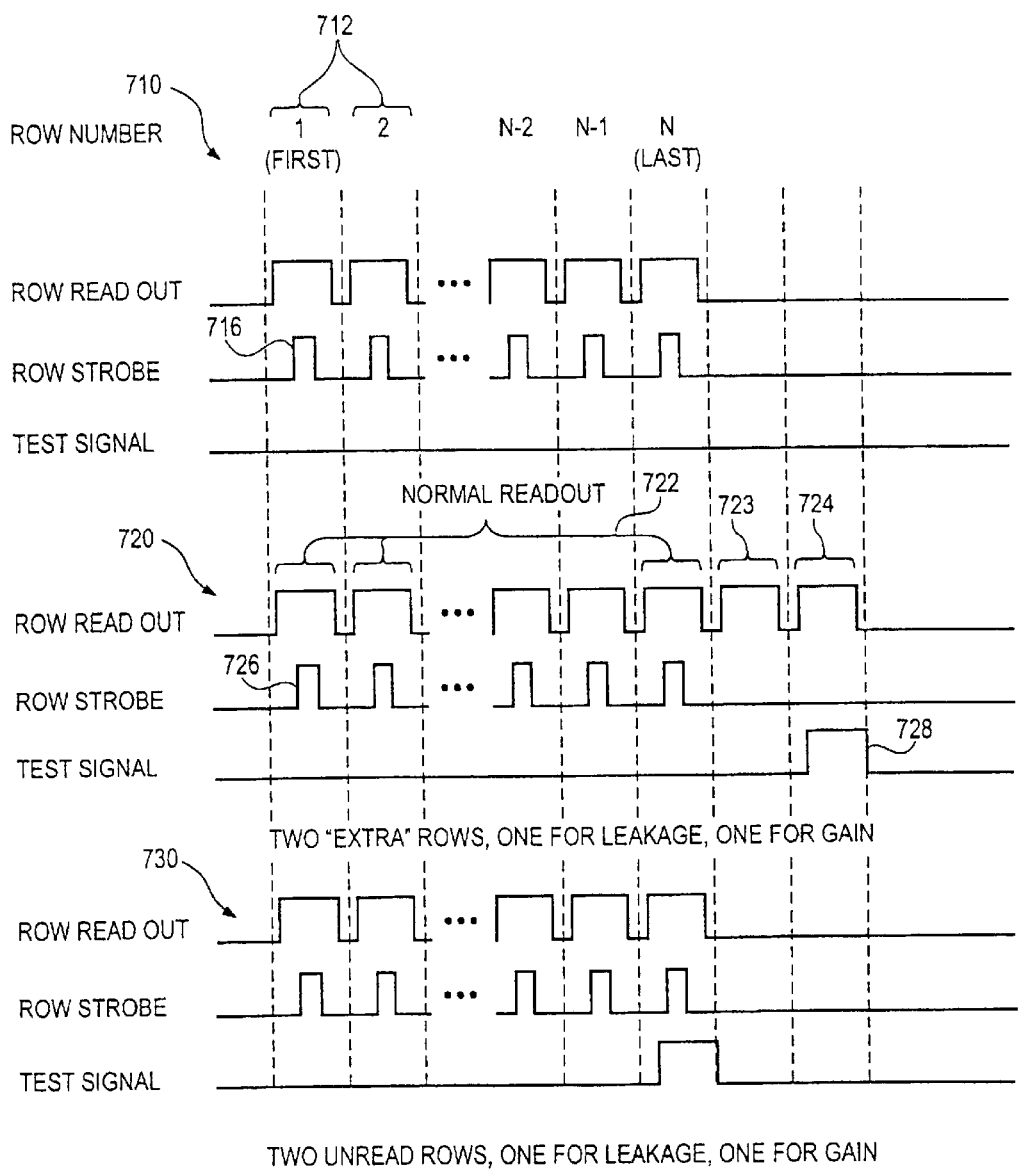

METHOD AND APPARATUS FOR CORRECTING ELECTRONIC OFFSET AND GAIN VARIATIONS IN A SOLID STATE X-RAY DETECTOR

CROSS REFERENCE TO RELATED APPLICATIONS (if applicable)

Not applicable.

STATEMENT REGARDING FEDERALLY SPONSORED RESEARCH & DEVELOPMENT (if applicable)

Not Applicable.

BACKGROUND OF THE INVENTION

The preferred embodiments of the present invention generally relate to medical diagnostic imaging systems, and in particular relates to a method and apparatus for correcting electronic offset and gain variations in medical imaging systems employing solid state detectors.

X-ray imaging has long been an accepted medical diagnostic tool. Xray imaging systems are commonly used to capture, as examples, thoracic, cervical, spinal, cranial, and abdominal images that often include information necessary for a doctor to make an accurate diagnosis. X-ray imaging systems typically include an xray source and an x-ray sensor. When having a thoracic x-ray image taken, for example, a patient stands with his or her chest against the x-ray sensor as an x-ray technologist positions the x-ray sensor and the x-ray source at an appropriate height. X-rays produced by the source travel through the patient's chest, and the x-ray sensor then detects the x-ray energy generated by the source and attenuated to various degrees by different parts of the body. An associated control system obtains the detected x-ray energy from the x-ray sensor and prepares a corresponding diagnostic image on a display.

The x-ray sensor may be a conventional screen/film configuration, in which the screen converts the x-rays to light that exposes the film. The x-ray sensor may also be a solid state digital image detector. Digital detectors afford a significantly greater dynamic range than conventional screen/film configurations.

One embodiment of a solid state digital x-ray detector may be comprised of a panel of semiconductor FETs and photodiodes. The FETs and photodiodes in the panel are typically arranged in rows (scan lines) and columns (data lines). A FET controller controls the order in which the FETs are turned on and off. The FETs are typically turned on, or activated, in rows. When the FETs are turned on, charge to establish the FET channel is drawn into the FET from both the source and the drain of the transistor. Due to the imperfect nature of the amorphous silicon FETs, the charge is retained temporarily when the FET is turned off and bleeds out, decaying, over time. which corrupts desired the signal in the form of an offset. The source of each FET is connected to a photodiode. The drain of each FET is connected to readout electronics via data lines. Each photodiode integrates the light signal and discharges energy in proportion to the x-rays absorbed by the detector. The gates of the FETs are connected to the FET controller. The FET controller allows signals discharged from the panel of photodiodes to be read in an orderly fashion. The readout electronics convert the signals discharged from photodiodes. The energy discharged by the photodiodes in the detector and converted by the readout electronics is used by an acquisition system to activate pixels in the displayed digital diagnostic image. The panel of FETs and photodiodes is typically scanned by row. The corresponding pixels in the digital diagnostic image are typically activated in rows.

The FETs in the x-ray detector act as switches to control the charging of the photodiodes. When a FET is open, an associated photodiode is isolated from the readout electronics. The associated photodiode is discharged during an x-ray exposure. When the FET is closed, the photodiode is recharged to an initial charge by the readout electronics. Light is emitted by a scintillator in response to x-rays absorbed from the source. The photodiodes sense the emitted light and are partially discharged. Thus, while the FETs are open, the photodiodes retain a charge representative of the x-ray dose. When a FET is closed, the voltage across the photodiode is restored to re-establish a desired voltage across the photodiode. The measured charge amount to re-establish the desired voltage becomes a measure of the x-ray dose integrated by the photodiode during the length of the x-ray exposure.

Readout electronics read the output signal from the x-ray detector panel. When the readout electronics are activated to read out the output signal from the x-ray detector panel, an electronic offset may be added to the resulting image. For example, some excess charge may "leak" from the readout electronics and add to the output signal. The charge leakage from the readout electronics may induce structured artifacts (including ghost images or distortions) in the x-ray image. The offset, such as charge leakage, from the readout electronics can be measured initially by acquiring a "dark" image. A "dark" image is a reading done without x-ray exposure. A "dark" image simply activates the FETs on the x-ray detector panel and reads the output signal through the readout electronics. Thus, a "dark" image may determine the offset, such as charge leakage, from the FET controller readout electronics. By subtracting the "dark" image pixel value from the actual "expose" x-ray image pixel value of a desired object, the offset (i.e., charge leakage) effects from sources such as the readout electronics may theoretically be eliminated.

Gain calibration is performed on the detector and electronics in order to provide gain correction coefficients for the x-ray image on a pixel by pixel basis. Gain calibration includes the sensitivity of the detector and the gain of the readout electronics. A flat field uniform x-ray exposure, with only an x-ray calibration phantom that uniformly attenuates the exposure, is used for gain calibration. Thus, it is desirable to perform gain calibration infrequently. After exposure, pixels in the gain calibration image are examined. Pixels that have a small response (less than the mean) are multiplied by a factor greater than one. Pixels that have a large response (greater than mean) are multiplied by a factor less than one. Pixels that exhibit a response below a given threshold are mapped out as "dead" pixels. Pixels above a second given threshold are also mapped out. Pixels above the second threshold will probably saturate too easily. Pixels that saturate too easily will probably not return any additional signal, exhibiting limited dynamic range.

X-ray images may be used for many purposes. For instance, internal defects in a target object may be detected. Additionally, changes in internal structure or alignment may be determined. Furthermore, the image may show the presence or absence of objects in the target. The information gained from x-ray imaging has applications in many fields, including medicine and manufacturing.

In any imaging system, x-ray or otherwise, image quality is of primary importance. In this regard, x-ray imaging systems that use digital or solid state image detectors ("digital x-ray systems") face certain unique difficulties. Difficulties in a digital x-ray image could include image artifacts, "ghost images," or distortions in the digital x-ray image. One source of difficulty faced by digital x-ray systems is offset (i.e., electronic leakage) and gain variation of readout electronics used in digital x-ray systems.

In an ideal image adjustment, offset correction may be performed as described above by subtracting the value of a "dark" image pixel from the value of a corresponding pixel in an exposed x-ray image. The result may be multiplied by a gain calibration coefficient described above. However, variation in gain and offset in readout electronics may affect offset correction and gain calibration.

Changes in temperature may have an effect on readout electronics. The output signals from the x-ray detector panel are very small. Since the output signals are very small, readout electronics are very sensitive. The sensitive readout electronics are susceptible to changes in temperature. Differences in temperature at different times will affect the signal read out by the readout electronics at the different times. Differences in temperature between gain calibration and at the time exposure data is read may cause variations in the gain to corrupt measurements taken when the image data is read from the x-ray detector panel. If the gain of the readout electronics changes between gain calibration and the x-ray image, the gain correction will be in error. Similarly, differences in temperature may cause changes in the offset, such as the amount of charge that "leaks," from the readout electronics when it is activated to read the output signal from the x-ray detector panel. As a result, the offset from the readout electronics in the x-ray image may differ from the offset from the readout electronics in the "dark" image. If the offsets from the readout electronics differ, the structured artifacts induced by the readout electronics offset (i.e., electronic leakage) will not be eliminated by subtracting the "dark" image from the actual "exposed" xray image of a desired object.

As noted above, the characteristics of digital image detectors inherently vary. Although there is a need to provide consistent and accurate image quality (and in particular, image gray scale resolution) within and across multiple medical diagnostic imaging systems, in the past there has been no automated technique for providing such consistency.

Thus, a need exists for a method and apparatus for correcting electronic offset and gain variations in a solid state x-ray detector.

BRIEF SUMMARY OF THE INVENTION

A preferred embodiment of the present invention provides a method and apparatus for correcting electronic offset and gain variations in solid state x-ray detectors. The method and apparatus include adding two or more rows to the end of a normal x-ray detector scan area. The additional rows may be outside the physical image area of a solid state x-ray detector. The additional rows then may be used to measure the "signal" induced by variations in electronic offset (such as electronic leakage) that may occur between "dark" image acquisition and x-ray image acquisition in a solid state x-ray detector. The additional rows also may be used to measure the variations in gain that may occur between gain calibration and x-ray image acquisition. The measurements may be made at the end of a detector scan. The signals induced by variations in electronic offset and gain might otherwise cause visible structured artifacts in the x-ray image.

An alternative preferred embodiment may use an existing solid state x-ray detector scan area and simply not activate two or more rows at the end of the x-ray detector scan area. This embodiment may reduce the image area covered by the scan.

BRIEF DESCRIPTION OF THE DRAWINGS

FIG. 7 shows a wave diagram demonstrating a method of acquiring an image according to a preferred embodiment of the present invention.

DETAILED DESCRIPTION OF THE INVENTION

Figure 1:
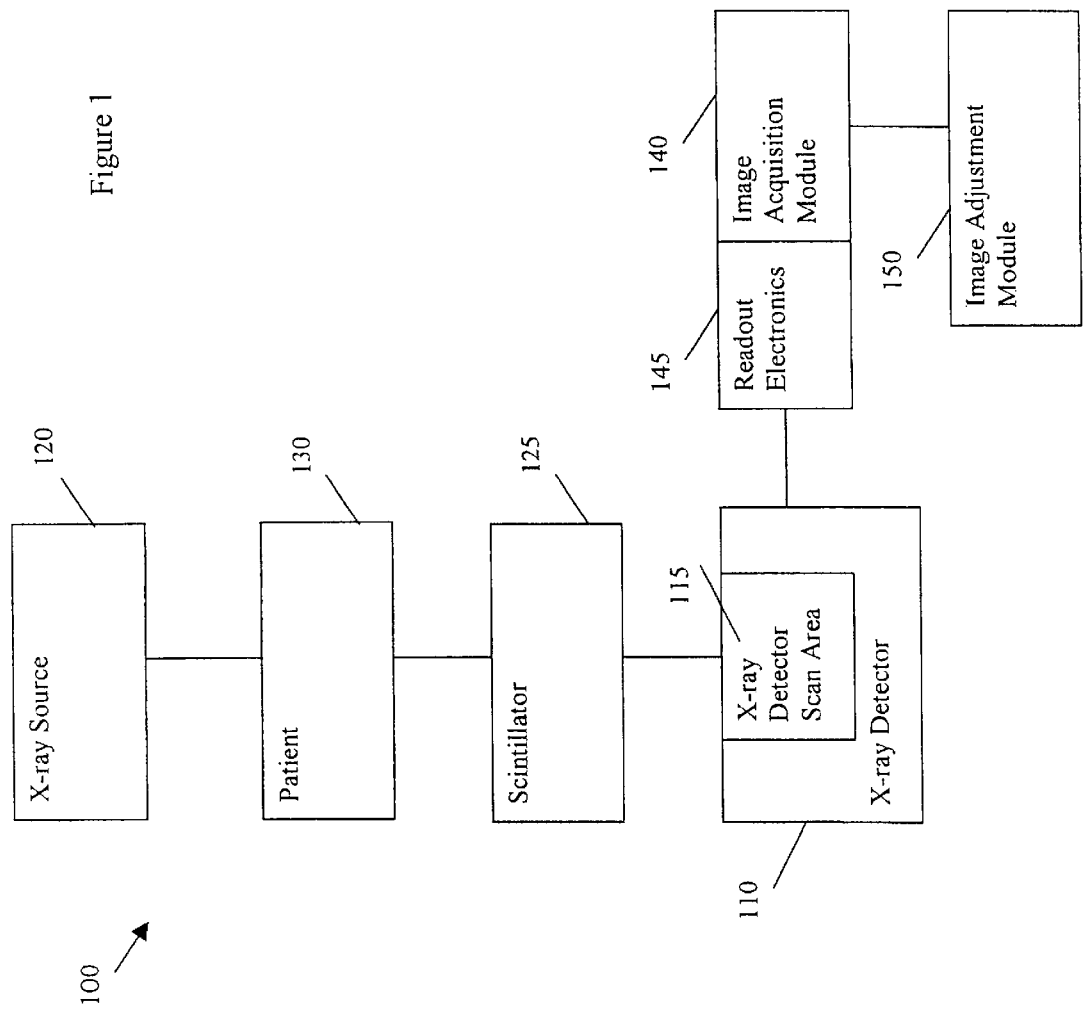
FIG. 1 illustrates a general medical diagnostic imaging system used in connection with a preferred embodiment of the present invention.

FIG. 1 illustrates a preferred embodiment of a medical diagnostic imaging system 100. The medical diagnostic imaging system 100 includes a plurality of subsystems. For the purposes of illustration only, the medical diagnostic imaging system 100 is described as an x-ray system. The medical diagnostic imaging system 100 includes subsystems, such as an x-ray detector 110, an x-ray detector scan area 115, an x-ray source 120, a scintillator 125, and a patient 130. The medical diagnostic imaging system 100 also includes an image acquisition module 140 and an image adjustment module 150. The image acquisition module 140 includes readout electronics 145.

The patient 130 is positioned in the medical diagnostic imaging system 100. In one exemplary system, an x-ray source 120 is positioned below the patient 130. The x-ray detector 110 is positioned above the patient 130. The scintillator 125 is positioned between the x-ray detector 110 and the patient 130. X-rays are transmitted from the x-ray source 120 through the patient 130 to the scintillator 125. The scintillator 125 emits light in response to the x-rays transmitted from the x-ray source 120 through the patient 130. The emitted light is transmitted to the x-ray detector 110 and the x-ray detector scan area 115.

Figure 2:
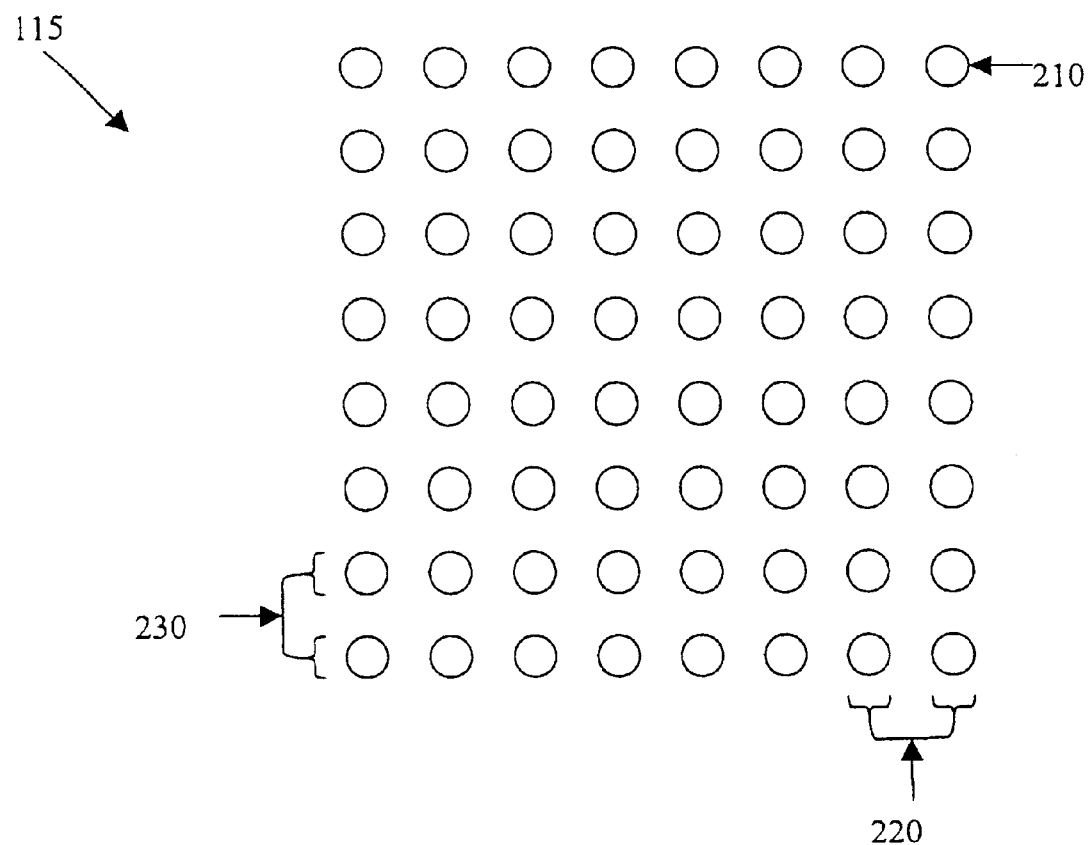
FIG. 2 illustrates a preferred embodiment of a solid state x-ray detector scan area.

FIG. 2 illustrates a preferred embodiment of a solid state x-ray detector scan area 15 within an x-ray detector 110. The x-ray detector scan area 115 is comprised of cells 210 corresponding to pixels in an x-ray image. Each cell 210 typically comprises a photodiode and a Field Effect Transistor (FET). The cells 210 may be arranged in columns 220 and rows 230. The cells 210 are controlled by scan lines along row 230 and read out by data lines along column 220. One or more cells 210 are uniquely mapped to one or more pixels in an x-ray image. The pixels are activated to produce the desired digital x-ray image of the patient 130.

Figure 3:
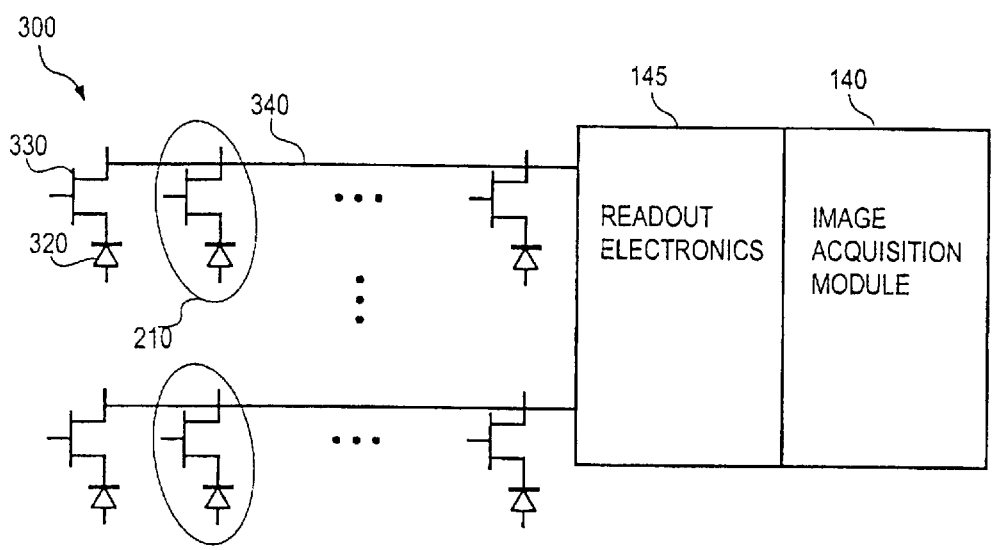
FIG. 3 illustrates a preferred embodiment of a solid state x-ray detector.

FIG. 3 illustrates a lower-level view of a preferred embodiment of a solid state x-ray detector scan area 115 within an x-ray detector 110. The x-ray detector scan area 115 is comprised of cells 210 comprising a photodiode 320 and a Field Effect Transistor (FET) 330. Data lines 340 connect the cells 210 to the readout electronics 145 of the image acquisition module 140.

Figure 4:
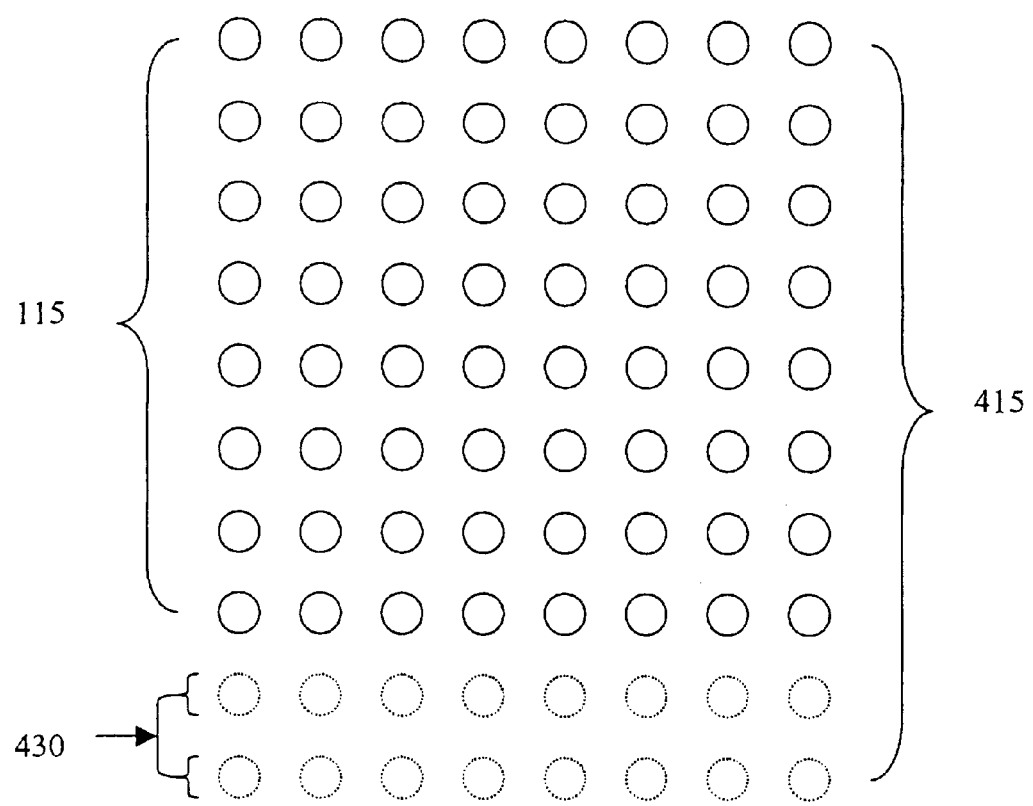
FIG. 4 illustrates a preferred embodiment of a solid state x-ray detector scan area with two additional rows for correction at the end of the x-ray detector scan area.

Through the readout electronics 145, the image acquisition module 140 acquires an x-ray image from the x-ray detector scan area 115 (See FIG. 3). In a preferred embodiment, the image acquisition module 140 may acquire more data than an image from an exposed detector section 115. In a preferred embodiment, shown in FIG. 4, the x-ray detector scan area 115 may be superficially enlarged by scanning additional phantom rows 430 after the end of the x-ray detector scan area 115 to form an enlarged x-ray detector scan area 415. The number of additional rows 430 may vary. Also, additional rows 430 may be located along one or both sides of the x-ray detector scan area 115, in addition to being located before or after the x-ray detector scan area 115. The image acquisition module 140 may acquire the image from the enlarged x-ray detector scan area 415.

Figure 5:
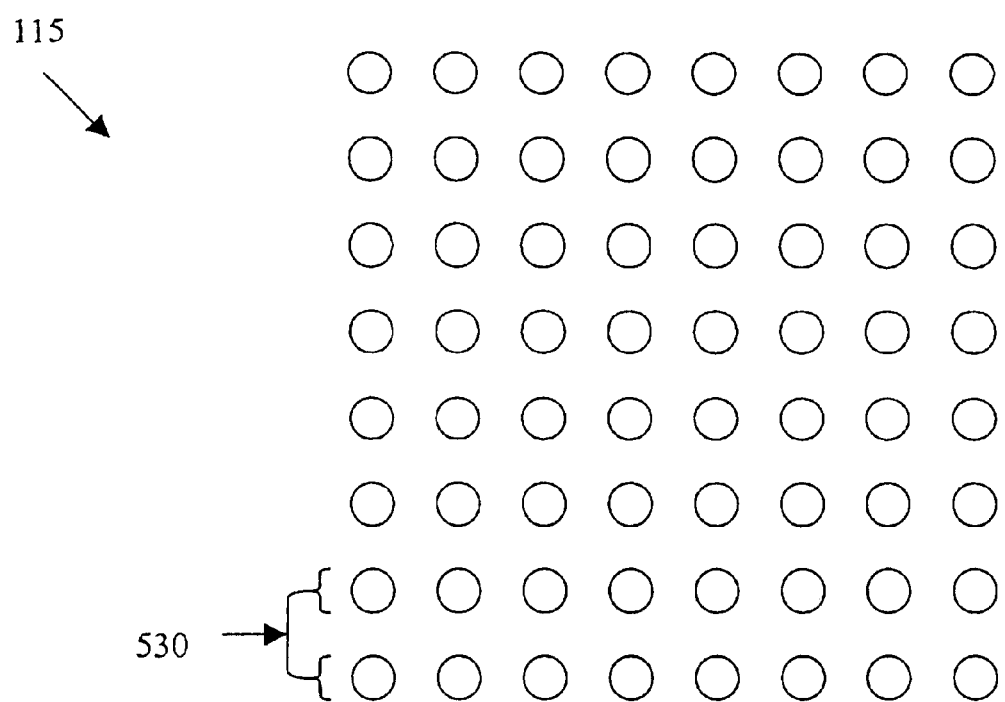
FIG. 5 illustrates a preferred embodiment of a solid state x-ray detector scan area with two rows dedicated for correction at the end of the x-ray detector scan area.

In another preferred embodiment, shown in FIG. 5, the x-ray detector scan area 115 may be reduced by two or more rows 530 at the end of the x-ray detector scan area 115 and/or by two or more rows along the front of the x-ray detector scan area 115. The rows dedicated in the normal x-ray detector scan area 115 may be used for correction of offset (such as electronic leakage) and gain variation in place of the additional rows 430 in another preferred embodiment. The image acquisition module 140 may acquire an x-ray image from the x-ray detector scan area 115.

The image acquisition module 140 may acquire an x-ray image from the x-ray detector scan area 115, 415 by receiving a signal through the readout electronics 145 from the data lines 340 from the cells 210 in the x-ray detector scan area 115, 415. The signal from the data lines 340 may be generated by the discharge of photodiodes 320. The photodiodes 320 may be discharged as a result of the absorption of light by the photodiodes 320. The light may be emitted by the scintillator 125 directly above the photodiodes 320 in response to absorption of x-ray energy by the scintillator 125. The FETs 330 allow the charge stored by the photodiodes 320 to travel as a signal through the data lines 340 from the readout electronics 145. The FETs 330 may be actuated by the readout electronics 145 in the image acquisition module 140. The signal received by the image acquisition module 140 through the data lines 340 may include structure artifacts (including ghost images and distortion) produced by the electronic offset (i.e., electronic leakage) and gain variations of the readout electronics 145.

The image adjustment module 150 receives the acquired image from the image acquisition module 140. The image adjustment module 150 corrects the structured artifacts induced in the x-ray image by the readout electronics 145. The structured artifacts in the x-ray image may be induced by variation in electronic offset (such as electronic leakage) and/or variation in gain in the readout electronics 145. In a preferred embodiment, the additional rows scanned at the end of the x-ray detector scan area 115, 415 are utilized by the image adjustment module 150 to correct structured artifacts in the x-ray image induced by electronic offset and gain variations from the readout electronics 145. In an alternative preferred embodiment, the rows dedicated at the end of the normal x-ray detector scan area 115, 415 are utilized by the image adjustment module 150 to correct structured artifacts in the x-ray image induced by electronic offset and gain variations from the readout electronics 145.

Figure 6:
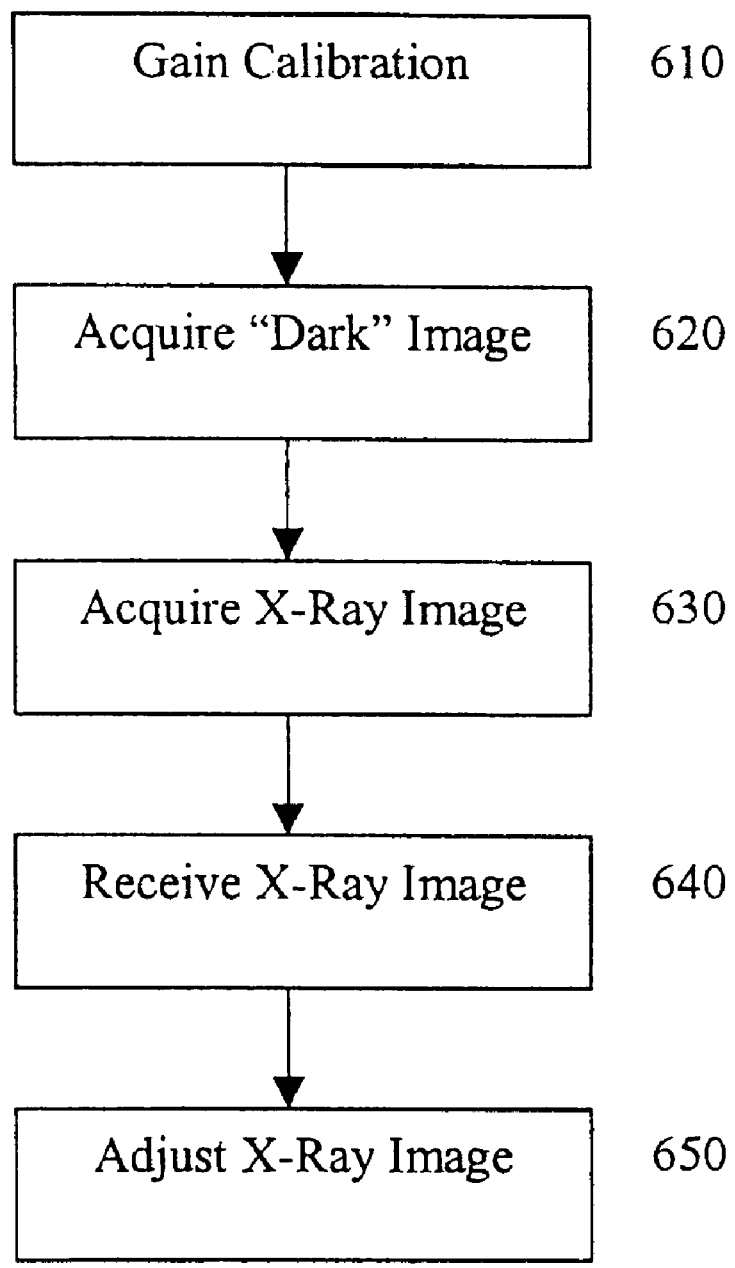
FIG. 6 illustrates a flow diagram of a preferred embodiment for correcting electronic offset and gain variations in a solid state x-ray detector.

Turning now to FIG. 6, the figure illustrates a flow diagram 600 for a preferred embodiment for correcting the offset induced in a medical diagnostic imaging system. In step 610, the image acquisition module 140 acquires a gain calibration measurement from the readout electronics 145. In a preferred embodiment, the gain calibration measurement is obtained first. Preferably, the gain calibration image is obtained once for the x-ray exposure. An x-ray exposure is taken for a gain calibration image. Pixels in the gain calibration image are examined to determine gain calibration coefficients. Pixels that exhibit a response less than a mean response value are multiplied by a gain calibration coefficient greater than one. Pixels that exhibit a response greater than a mean response value are multiplied by a gain calibration coefficient less than one. If a pixel exhibits a response below a certain threshold, it does not return enough signal and is mapped out of the image. A pixel that exhibits a response above a certain threshold saturates too easily and will probably not return additional signal. Such pixels above the certain threshold are also mapped out of the image.

In step 620, the image acquisition module 140 acquires a "dark" image from the x-ray detector scan area 115, 415. A "dark" image is obtained from a reading taken without x-rays. A scan for a "dark" image activates the FETs 330 in the x-ray detector scan area 115, 415 and reads the output signal through the readout electronics 145. Thus, a "dark" image may determine the initial electronic offset (for example, the initial electronic leakage) from the readout electronics 145. By subtracting the "dark" image from the actual "exposed" x-ray image of a desired object, the initial electronic offset effects from the readout electronics 145 may theoretically be eliminated.

In step 630, the image acquisition module 140 acquires an x-ray image from the x-ray detector scan area 115, 415. The image contains structured artifacts from variations in electronic offset (e.g., leakage) and gain in the readout electronics 145. The x-ray image is read row by row by the image acquisition module 140 through the readout electronics 145 from the x-ray detector scan area 115, 415 using data lines 340 from cells 210 in the x-ray detector scan area 115, 415. In a preferred embodiment of the present invention, the image acquisition module 140 acquires two additional rows 430 at the end of the image scan. The additional rows 430 do not represent the object being scanned. The additional rows 430 indicate the structured artifacts induced by variations in electronic offset and gain from the readout electronics 145. In another preferred embodiment of the present invention, the image acquisition module 140 dedicates two rows 530 at the end of the x-ray detector scan area 115, 415 to electronic offset and gain measurement, thus reducing the overall size of the acquired image.

During operation, the image acquisition module 140 performs consecutive or successive scans (read operations) of each row 230 of cells 210 in the x-ray detector scan area 115, 415. First, the image acquisition module 140 performs a row by row scan of each row 230 in the scanned image area of the x-ray detector scan area 115. During the row by row scan of each row 230 in the scanned image area of the x-ray detector scan area 115, the image acquisition module 140 obtains image exposure data for each cell 210 in the x-ray detector scan area 115. The image acquisition module 140 then may scan two or more rows 430, 530 outside (e.g., after) the scanned image area of the x-ray detector scan area 115. The image acquisition module 140 acquires electronic offset (e.g., leakage) measurements from at least the first of the rows 430, 530 scanned outside the scanned image area of the x-ray detector scan area 115. The image acquisition module 140 acquires gain measurements from at least the second of the rows 430, 530 scanned outside the scanned image area of the x-ray detector scan area 115.

In one embodiment, charge retention current may affect offset measurements acquired from the x-ray detector scan area 115 by the image acquisition module 140. The magnitude of the charge retention current may be affected by the time at which the charge retention current is measured relative to the scan of the last row 230. Since the time between frames may vary, offset correction measurements may be acquired closely following the actuation of the last row (scan line) 230. Charge retention current may also affect the gain correction measurement. The gain correction measurements may be acquired at the end of a detector read out. If offset and gain correction measurements are made at the end of the detector read out as opposed to the beginning of the detector read out, the charge retention current offset may be larger than the charge retention current offset at the beginning of the detector read out. If offset and gain correction measurements are made at the end of the detector read out as opposed to the beginning of the detector read out, the charge retention current offset may be more constant from frame to frame than the charge retention current offset would be at the beginning of the detector read out.

In another embodiment, a switch may be added between each column (data line) 220 of the x-ray detector scan area 115 and the corresponding input 340 to the read out electronics 145. The switch may remove charge retention current as a source of offset error when the offset correction measurement is made. Normally the switches would all be closed. When the electronic offset measurements are made, using the "additional" offset row(s) 430, 530, the switches may be momentarily opened, interrupting the flow of charge retention current into the read out electronics 145. Once the additional offset measurement is complete, the switches may be closed. A test signal may be used to measure gain. In a preferred embodiment, the test signal employs parasitic capacitance elements of the detector 110, as described by U.S. Pat. No. 5,352,884. Since the test signal employs detector parasitic capacitance elements, the switches remain closed during the additional rain correction measurements.

FIG. 7 illustrates the scanning process performed by the image acquisition module 140 in step 630. Timing diagram 710 represents the traditional scanning method executed in a medical diagnostic imaging system 100. During each time slice 712, a row strobe 716 is activated. During a time slice 712, a row strobe 716 is activated for each row 230 in the x-ray detector scan area 115. During a time slice 712, the image acquisition module 140 reads the row 230 for which a row strobe 716 is activated. The scanning method may be performed on both the dark and exposed images.

Timing diagram 720 represents the scanning method executed in a preferred embodiment of an image acquisition module 140 in a medical diagnostic imaging system 100. During each time slice 722, a row strobe 726 is activated for each row 230 in the x-ray detector scan area 115. During a time slice 722, the image acquisition module 140 reads the row 230 for which a row strobe 726 is activated. This row scan is a data acquisition scan and obtains image exposure data for each cell 210 in the row 230. The image data represents an x-ray dose or amount of exposure received by an associated cell 210. The image acquisition module 140 obtains image exposure data for each cell 210 that is used to determine the intensity of a corresponding pixel on the digital image display. During each time slice 723, a new row strobe 726 is not activated. During a time slice 723, the image acquisition module 140 reads the first "extra" row 430 to obtain electronic offset correction data for cells 210 in the row 430. During each time slice 724, a new row strobe 726 is not activated. During a time slice 724, a test signal 728 is activated. The image acquisition module 140 reads the second extra row 430 to obtain gain data induced by the test signal 728 for the second extra row 430. The scanning method may be performed on both the dark and exposed images.

Timing diagram 730 represents the scanning method executed in another preferred embodiment of an image acquisition module 140 in a medical diagnostic imaging system 100. The scanning method used in timing diagram 730 is similar to the scanning method used in timing diagram 720 but uses dedicated rows 530 in the x-ray detector scan area 115. The scanning method may be performed on both the dark and exposed images.

In step 640, the image adjustment module 150 receives x-ray image data from the image acquisition module 140. The image includes the extra rows 430, 530 at the end of the image scan dedicated to correction for electronic offset (e.g., electronic leakage) and gain variations. In a preferred embodiment, the x-ray image data includes one row of offset variation data and one row of gain variation data with the image exposure data. The offset variation data is used to adjust image offset. The gain variation data is used to adjust gain calibration. The adjusts may be performed during the imaging process. The image adjustment module 150 analyzes the image on a pixel by pixel basis, according to row and column. In step 650, the image adjustment module 150 calculates the image data value for a pixel in the image. For each pixel, an offset corrected image data value (OC) is obtained by subtracting offset image data (OD) from an exposure data value (ED) taken from the x-ray image. The result is multiplied by a gain calibration coefficient (G) to produce the image data value (ID).

In a preferred embodiment, the OC is calculated from ED and offset data (OD). The offset corrected image data is equal to the exposure data minus the offset data $\{OC_{ij}=ED_{ij}-OD_{ij}-(ED_{eorj}-OD_{eorj})\}$. In the offset correction equation, i indicates the row 230, 430, 530, and j indicates the column 220. The row index i only indexes to the last real row 230 read. The value $ED_{ij}$ corresponds to the exposure data for the pixel at ij from the exposed x-ray image. The value $OD_{ij}$ corresponds to the offset data from the corresponding pixel in the "dark" image. Both the "dark" image and exposure image contain the extra rows 430, 530 used for correction. The values $ED_{eorj}$ and $OD_{eorj}$ correspond to exposure data and offset data from the extra offset row (eor) common to column j in the exposed x-ray image.

In a preferred embodiment, OC is multiplied by a gain calibration coefficient (G) to produce the image data value (ID) for a pixel $\{ID_{ij}=OC_{ij}*G_{ij}*((GD_{egrj}-GD_{eorj})/(ED_{egrj}-ED_{eorj}))\}$. $OC_{ij}$ data value obtained above. $G_{ij}$ corresponds to the initial gain calibration factor for the pixel. The initial gain calibration factor may be obtained according to typical gain calibration techniques. GD represents gain calibration data. $GD_{egrj}$ corresponds to gain calibration data for the extra gain row (egr). $ED_{egrj}$ corresponds to exposure data for the extra gain row. $GD_{eorj}$ corresponds to gain calibration data for the extra offset row. $ED_{eorj}$ corresponds to exposure data for the extra offset row.

Thus, the present invention provides a fairly simple solution to what has become a serious degradation issue for solid state x-ray detectors. The method and apparatus for correcting electronic offset and gain variations induced by readout electronics in a solid state x-ray detector may improve the design of new medical diagnostic imaging systems and may preserve existing medical diagnostic imaging systems through offset correction. The present invention may be easily implemented and does not necessarily require a change to existing hardware.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for generating a medical diagnostic image acquired by a detector in a medical diagnostic imaging system comprising:

calibrating a detector to obtain at least one calibration data set;

exposing the detector to an energy source to form an exposed detector section including an exposed patient subsection;

measuring at least first and second data sets generated by the detector, one of said at least first and second data sets being representative of variation data from at least a portion of said exposed detector section outside said exposed patient subsection and one of said at least first and second data sets being representative of image exposure data from at least a portion of said exposed patient subsection; and generating a medical diagnostic image based on said exposed patient subsection and a relation between said at least first and second data sets and said calibration data set.

2. The method of claim 1 wherein said step of exposing a detector to an energy source comprises exposing said detector to x-ray energy.

3. The method of claim 1 wherein said first and second data sets comprise an image exposure data set and a variation data set.

4. The method of claim 3 wherein said variation data set includes a measure of offset.

5. The method of claim 3 wherein said variation data set includes a measure of electronic gain.

6. The method of claim 4 wherein said offset includes electronic leakage.

7. The method of claim 3 wherein said step of measuring at least first and second data sets comprises measuring said at least a portion of said exposed detector section outside said exposed patient image for said variation data set and measuring said at least a portion of said exposed patient image for said image exposure data set.

8. The method of claim 1 wherein said measuring step comprises measuring at least first, second, and third data sets generated by the detector, one of said at least first, second, and third data sets being representative of at least a portion of said exposed detector section outside said exposed patient subsection and one of said at least first, second, and third data sets being representative of at least a portion of said exposed patient subsection.

9. The method of claim 8 wherein said first data set comprises an image exposure data set, said second data set comprises an offset data set, and said third data set comprises a gain data set.

10. The method of claim 9 wherein said offset data set comprises an electronic leakage data set.

11. The method of claim 1 wherein said step of generating said medical diagnostic image comprises subtracting a value from said first data set from a corresponding value in said second data set.

12. The method of claim 1 wherein said step of generating a medical diagnostic image comprises activating pixels in a digital display according to said measurements in said first and second data sets.

13. The method of claim 3 wherein said step of generating said medical diagnostic image comprises subtracting a value from said calibration data set from a corresponding value in said variation data set and subtracting the difference from a corresponding value in said image exposure data set.

14. The method of claim 3 wherein said step of generating said medical diagnostic image comprises taking a ratio between a value from said calibration data set and a corresponding value in said variation data set and multiplying the result by a corresponding value in said image exposure data set.

15. A detector subsystem for acquiring an image comprising:

a panel being exposed to energy representative of an object and energy outside of said object, said panel formed of an array of cells detecting discrete amounts of energy; and a scanner for reading data sets, each of which is representative of an amount of energy detected by a cell; said scanner reading a calibration data set; said scanner reading at least first and second data sets before, during, or after said panel being exposed to said energy; one of said at least first and second data sets read from at least a portion of said object to represent image exposure data and one of said at least first and second data sets read from at least a portion of said outside of said object to represent variation data; said scanner using a reader to read said calibration data set and said at least first and second data sets; said scanner producing an output based on a relation between said at least first and second data sets and said calibration data set.

16. The subsystem of claim 15 wherein said array of cells comprises:

an array of photodiodes detecting photons representative of said discrete amounts of energy; and an array of Field Effect Transistors switchably interconnecting said photodiodes and said scanner.

17. The subsystem of claim 15 wherein said first and second data sets comprise an image exposure data set and a variation data set.

18. The subsystem of claim 17 wherein said variation data set includes electronic gain data.

19. The subsystem of claim 17 wherein said variation data set includes offset data.

20. The subsystem of claim 19 wherein said offset data includes electronic leakage data.

21. The subsystem of claim 17 wherein said scanner reads said first data set from at least a portion of said panel with said object for said image exposure data set and said scanner reads said second data set from at least a portion of said panel outside said object for said variation data set.

22. A medical diagnostic imaging system, comprising:
- a detector for detecting an energy pattern emanating from a patient; said detector having an array of discrete collecting elements discharging in proportion to an amount of detected energy both from said patient and outside said patient;
- an image acquisition module restoring and measuring a charge stored on said collecting elements, said image acquisition module having readout electronics to measure said charge restored on said collecting elements; and
- said image acquisition module scanning said detector during at least a first pass to obtain calibration data representative of an energy characteristic of said detector and readout electronics, scanning said collecting elements during at least a second pass to obtain image exposure data representative of said energy pattern from said patient, and scanning said collecting elements to obtain variation data representative of an energy characteristic of said readout electronics.

23. The system of claim 22 further comprising:
- an image adjustment module correcting said image exposure data using said calibration data and said variation data to minimize the effect of said energy characteristic of said readout electronics.

24. The system of claim 22 wherein said detector further comprises:
- an array of Field Effect Transistors switchably interconnecting said collecting elements and said image acquisition module.

25. The system of claim 24 wherein said energy characteristic of said readout electronics includes electronic offset drift.

26. The system of claim 25 wherein said electronic offset includes electronic leakage drift.

27. The system of claim 24 wherein said energy characteristic of said readout electronics includes electronic gain drift.

28. The system of claim 22 wherein said collecting elements comprise photodiodes.

29. The system of claim 22 wherein said energy pattern is an x-ray energy pattern.

30. The system of claim 22 further comprising a third pass at the end of an image exposure to obtain variation data at a constant charge retention.

31. The system of claim 22 further comprising a switch, said switch isolating said detector and said readout electronics.

* * * * *